United States Patent
Nardeo et al.

(10) Patent No.: US 8,414,537 B2
(45) Date of Patent: Apr. 9, 2013

(54) INTRODUCER SHEATH ASSEMBLY WITH HUB

(75) Inventors: Mahase Nardeo, Collegeville, PA (US); Trevor Spence, Lancaster, PA (US)

(73) Assignee: Medical Components, Inc., Harleysville, PA (US)

( * ) Notice: Subject to any disclaimer, the term of this patent is extended or adjusted under 35 U.S.C. 154(b) by 21 days.

(21) Appl. No.: 12/976,294

(22) Filed: Dec. 22, 2010

(65) Prior Publication Data

US 2011/0098649 A1 Apr. 28, 2011

Related U.S. Application Data

(62) Division of application No. 12/360,614, filed on Jan. 27, 2009.

(60) Provisional application No. 61/062,714, filed on Jan. 29, 2008.

(51) Int. Cl.
*A61M 5/178* (2006.01)
*A61M 25/00* (2006.01)

(52) U.S. Cl. ............ 604/164.05; 604/164.01; 604/264

(58) Field of Classification Search ............ 604/264, 604/160, 161, 165.01, 164.01, 191, 193–194, 604/198–199
See application file for complete search history.

(56) References Cited

U.S. PATENT DOCUMENTS

| | | | |
|---|---|---|---|
| 3,720,210 A | 3/1973 | Diettrich | |
| 3,903,887 A | 9/1975 | Antoshkiw | |
| 4,306,562 A | 12/1981 | Osborne | |
| 4,581,025 A | 4/1986 | Timmermans | |
| 4,596,559 A | 6/1986 | Fleischhacker | |
| 4,772,266 A | 9/1988 | Groshong | |
| 5,290,249 A * | 3/1994 | Foster et al. | ............ 604/174 |
| 5,935,501 A | 8/1999 | Andrews et al. | |
| 6,083,207 A | 7/2000 | Heck | |
| 6,692,464 B2 | 2/2004 | Graf | |
| 6,712,791 B2 | 3/2004 | Lui et al. | |

(Continued)

FOREIGN PATENT DOCUMENTS

FR 2041652 1/1971

OTHER PUBLICATIONS

Brochure, "FlowGuard TM Valved Peelable Venous Introducer": Enpath Medical, Inc.; 2009 (1 page).

(Continued)

*Primary Examiner* — Nicholas Lucchesi
*Assistant Examiner* — Rebecca E Eisenberg
(74) *Attorney, Agent, or Firm* — Glenn M. Massina, Esq.; Fox Rothschild LLP

(57) ABSTRACT

A tearaway introducer sheath assembly (10) for use in implantation of a catheter into a patient, having an elongated polytetrafluoroethylene sheath tube (12) and a proximal polyethylene hub component (16). The hub comprises two halves (22) insert molded about the sheath tube proximal end and joined to each other by frangible webs (28) enabling manual splitting. At least one pair of opposed holes (42) is formed through the tube proximal end portion 44, and a polyethylene liner (46) is inserted into the tube's proximal end portion. The polyethylene flows into the at least one pair of holes (42) to fuse with the liner, establishing a pair of physical joints (50') integrally joining the liner (46) to a respective hub half (22). Upon manual splitting of the hub halves, the sheath tube easily splits along its length as a result of a property of the polytetrafluoroethylene material.

23 Claims, 4 Drawing Sheets

U.S. PATENT DOCUMENTS

| | | |
|---|---|---|
| 6,796,991 B2 | 9/2004 | Nardeo |
| 6,887,417 B1 | 5/2005 | Gawreluk et al. |
| 7,422,571 B2 | 9/2008 | Schweikert et al. |
| 2003/0050604 A1 | 3/2003 | Lui et al. |
| 2003/0135197 A1 | 7/2003 | Wang et al. |
| 2004/0254534 A1 | 12/2004 | Bjorkman et al. |
| 2005/0033237 A1 | 2/2005 | Fentress et al. |
| 2005/0049628 A1 * | 3/2005 | Schweikert et al. .......... 606/198 |
| 2005/0059958 A1 | 3/2005 | Lessard et al. |
| 2006/0052749 A1 | 3/2006 | Moyer |
| 2007/0073310 A1 | 3/2007 | Pal et al. |
| 2007/0250150 A1 | 10/2007 | Pal et al. |
| 2008/0082120 A1 | 4/2008 | Mauch et al. |

OTHER PUBLICATIONS

Photographs, "FlowGuard" Product of Enpath Medical, Inc. (date unknown) (4 sheets).

International Search Report and Written Opinion dated Sep. 4, 2009; PCT Application No. PCT/US2009/032121) (12 pages).

International Preliminary Report on Patentability dated Jan. 28, 2011; PCT Application No. PCT/US09/032121 (8 pages).

* cited by examiner

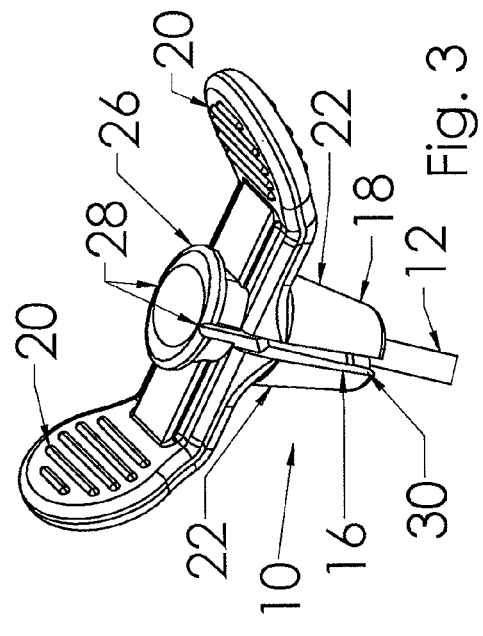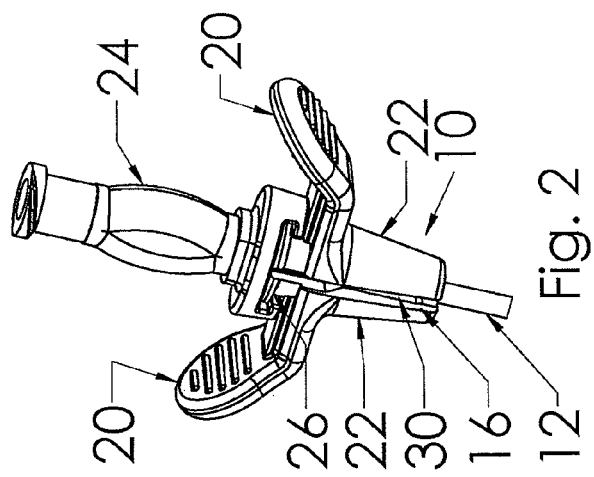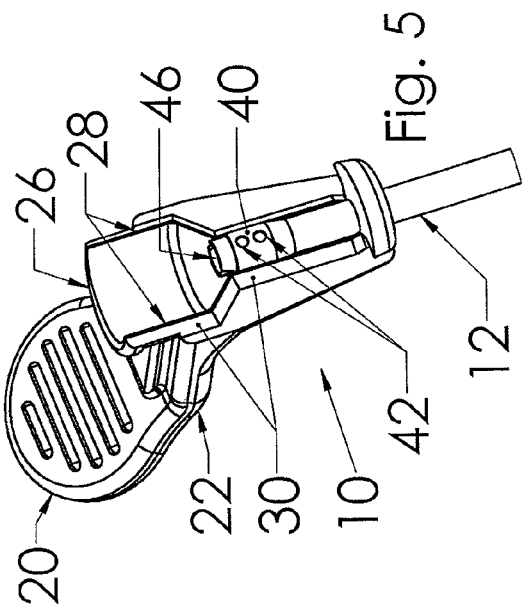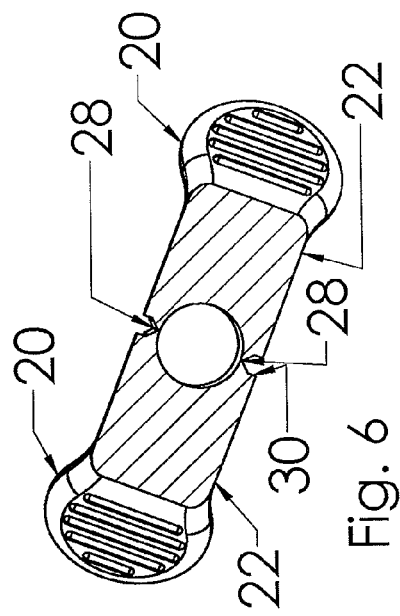

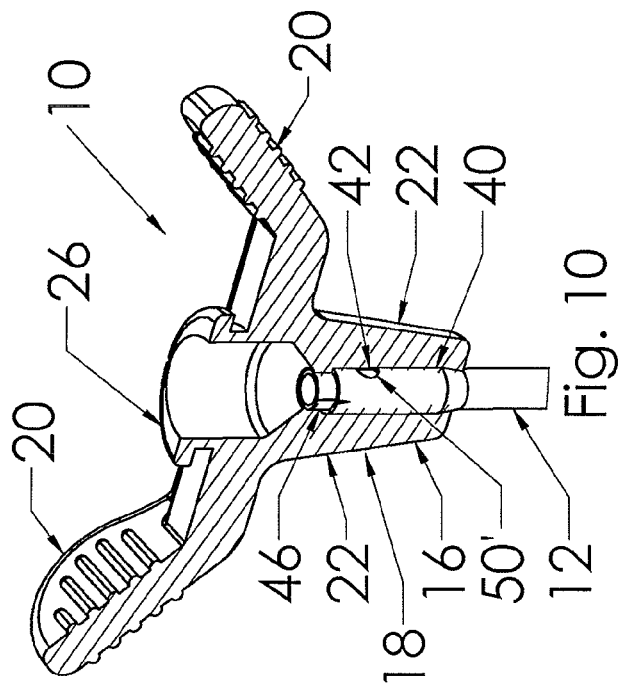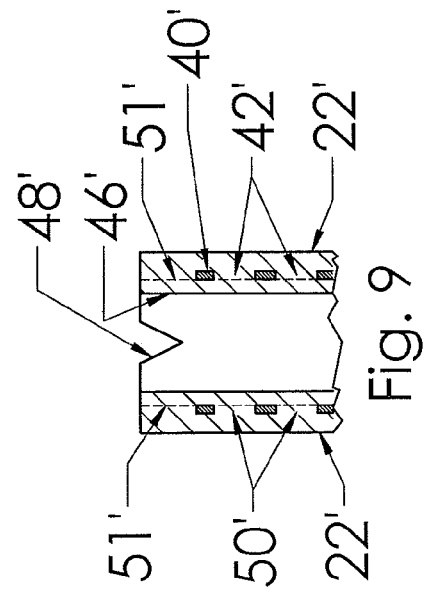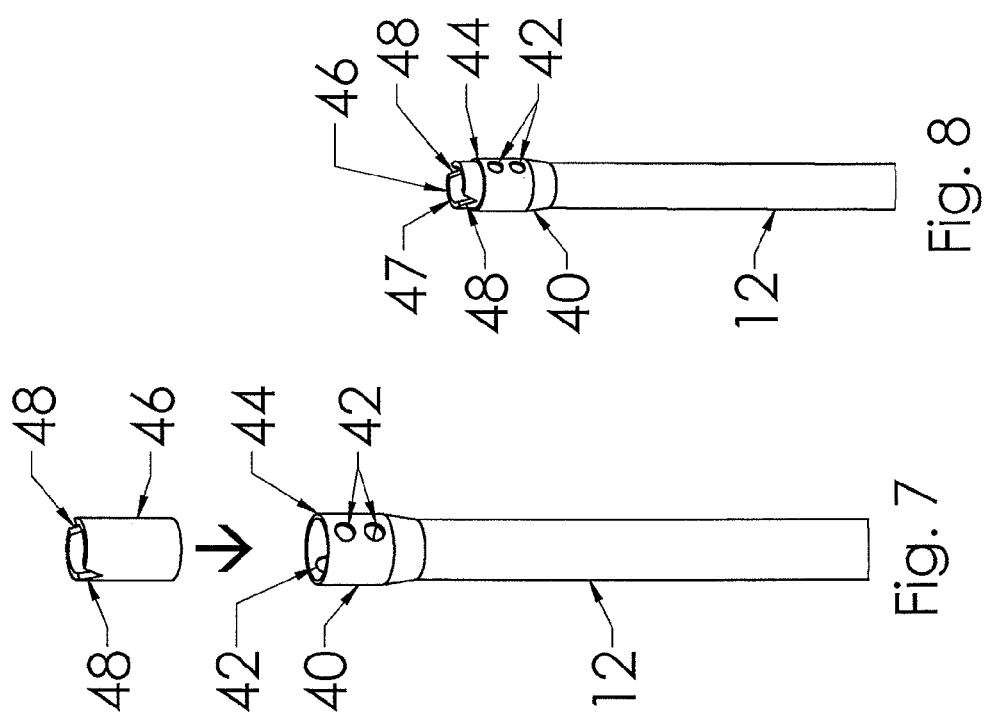

INTRODUCER SHEATH ASSEMBLY WITH HUB

CROSS-REFERENCE TO RELATED APPLICATIONS

This application is a Divisional application of U.S. patent application Ser. No. 12/360,614 filed Jan. 27, 2009, which claims priority from U.S. Provisional Patent Application Ser. No. 61/062,714, filed Jan. 29, 2008.

FIELD OF THE INVENTION

This relates to the field of medical devices, and more particularly to flexible medical tubing and components affixed thereto.

BACKGROUND OF THE INVENTION

Catheters are often used for the delivery and withdrawal of fluids to and from a blood vessel in a patient, respectively. The fluids may be medication that is administered to the patient, or blood that is withdrawn from the patient. The catheter may also be used for hemodialysis, in which blood is withdrawn from the patient, purified and returned simultaneously through respective lumens of the catheter, and much of the catheter remains within the patient's vasculature for an extended period of time for repeated treatments.

Typically, to insert a catheter into a blood vessel, the blood vessel is located by known methods. An aspirating needle is inserted into the vessel to confirm placement within the vessel. A guide wire is then inserted through a proximal end of the aspirating needle and into the vessel. The aspirating needle is withdrawn by sliding the needle proximally over the guide wire, leaving the guide wire within the vessel. If a catheter with a sufficiently hard wall is being used, the catheter may be slid over the guide wire, directly into the vessel.

However, for some catheters, particularly soft walled catheters, a dilator is required to dilate the vessel at the insertion point in order to accommodate the insertion of the catheter. The dilator is typically inserted into a sheath and initially used as a dilator and sheath assembly. The assembly is inserted into the vessel over the guide wire and the dilator is used to dilate the insertion opening in the vessel wall. After the insertion opening is dilated, the dilator and the guide wire are removed from the vessel by removing both the dilator and the guide wire proximally from the sheath. The sheath remains in the vessel to accommodate insertion of the catheter through the sheath and into the blood vessel.

Additionally, splittable introducer sheaths are known, wherein the sheath can be easily removed from around a catheter assembly inserted thereinto and into the patient's vasculature. Typically, such assemblies include manually grippable tabs or wings at the proximal end of the sheath hub that can be pried apart to initiate splitting of the hub and the attached sheath tube apart while simultaneously pulling it proximally along the catheter and out of the patient.

Conventionally, introducer sheaths have hubs affixed to their proximal ends to which the dilator hub is locked during preparation of the vessel insertion opening. It has become desired for the sheath to be of polytetrafluoroethylene, while the hub material is a different plastic material such as polyethylene. It is known the polytetrafluoroethylene, or PTFE, is notoriously difficult to bond to other plastic materials, so it remains problematic to configure methods and manners of securing the hub to the sheath.

It is desired to provide a simplified method of securing a hub to a PTFE sheath proximal end.

It is further desirable to provide a simplified method of securing a hub to a PTFE sheath proximal end, where the introducer sheath assembly is splittable and the hub component halves must remain affixed to respective halves of the sheath during splitting.

BRIEF SUMMARY OF THE INVENTION

Briefly, the present invention provides a method of forming an assured joint between a tube of a first plastic material and a component of a second plastic material incompatible with the first plastic material. The method comprises the steps of: providing a tube of a first plastic material and having a proximal end through which are formed at least one pair of holes on opposed sides and generally aligned with each other; providing an interior lining portion of a second plastic material different from the first material, such as a preformed liner being inserted into the tube proximal end for the liner to underlie the at least one pair of holes; and molding around the tube proximal end a component of the second plastic material or a third material at least compatible with the second material such that a bond would form therebetween during molding, whereby the material of the component protrudes through the at least one pair of holes and fuses or bonds to the material of the liner, thereby establishing joints that extend through the holes of the tube and affix both the component and the liner to the tube.

In one practical embodiment, the method provides an assured joint of an introducer sheath tube of polytetrafluoroethylene (PTFE) and a liner and a hub component (or components) of a different plastic such as polyethylene.

It may be desirable to provide an expanded inner diameter to the tube's proximal end, such that the liner may have an inner diameter substantially equal to the inner diameter of the remainder of the tube. Optionally, an array of two or more holes may be provided along each side of the tube proximal end for a stronger joint between the component and the tube.

An introducer assembly of the present invention may be made using the present inventive method where the hub component is molded to the sheath tube proximal end, where the hub comprises two halves initially joined to each other at frangible seams along opposite sides of the sheath tube, such that the hub component can be easily split for easy removal of the introducer sheath assembly from a catheter after insertion into a patient. The sheath tube has at least one pair of holes adjacent the proximal end through which the hub halves are formed with joints extending through the sheath tube holes affixing them to a liner within the sheath tube, so that each hub half remains assuredly affixed to a respective side of the sheath tube. Also, preferably, the liner includes a proximal end portion protruding beyond the sheath tube proximal end to which the hub component integrally joins, as well, and may include notches into the proximal end to initiate eventual sheath assembly splitting. The introducer sheath tube has inherent lines of weakness, and additionally may have slits partially therealong, to continue the splitting entirely along the sheath tube, resulting from the PTFE material. Other sheath tube materials may be used but scoring of an opposed pair of seams therealong would expected to be provided to facilitate sheath tube splitting.

In an alternate method of the invention, a preformed liner is not utilized. Instead, the proximal end of the sheath tube is expanded as before, with at least one pair of opposed holes formed therethrough, and the proximal sheath end is placed into a mold. With appropriately adapted mandrels extending through the sheath tube, a relatively thin gap, optionally annular, is provided between the mandrel and the inner diameter of the expanded proximal sheath end at least adjacent to and underlying the opposed holes. When the hub component is molded to the sheath end, mold material flows through the opposed holes and into the gap, and preferably for a limited distance along the mandrel proximally of the sheath tube proximal end as well, thereby forming an inner liner thereafter integrally joined to the outer hub halves.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 2 is an enlarged isometric view of the proximal end of the assembly of FIG. 1 with a dilator removably secured thereto at the proximal end;

FIG. 3 is an enlarged view of the proximal end of the assembly of FIG. 1 showing the frangible webs between the hub halves and the related grooves associated with the frangible webs;

FIG. 5 is an enlarged view of the proximal end of the assembly of FIG. 4 with one hub half removed and in which the thin frangible web is shown sectioned;

FIG. 6 is an enlarged distally facing cross-sectioned view of the hub halves separate from the sheath tube, illustrating the frangible webs and related grooves;

FIGS. 7 and 8 are isometric views showing a liner being inserted into the sheath tube proximal end and then in position in the sheath proximal end;

FIG. 9 is a representation longitudinal view of the proximal end of the sheath tube and liner with a hub molded thereto to illustrate the joints that extend through the opposed holes;

FIG. 10 is an enlarged cross-sectional view of the introducer assembly of the present invention after molding of the hub component, in which the liner is seen protruding from the sheath tube joined to the hub component by joints extending through the opposed holes;

DETAILED DESCRIPTION OF THE INVENTION

Figure 1:
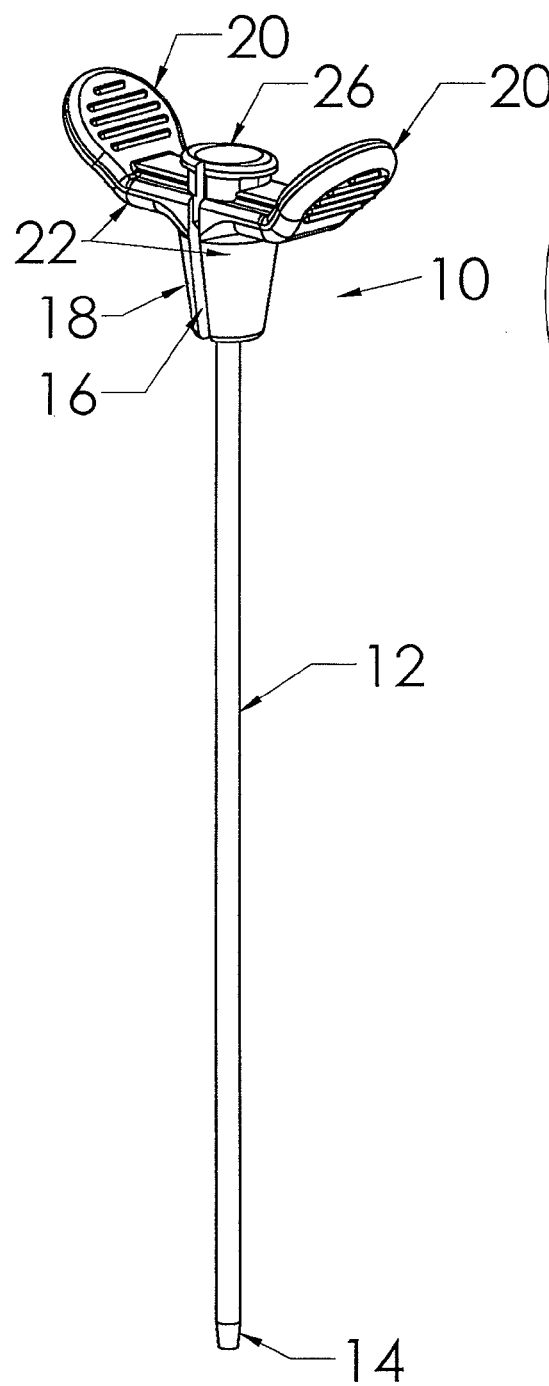
FIG. 1 is an isometric view of an introducer sheath assembly of the present invention.
Figure 4:
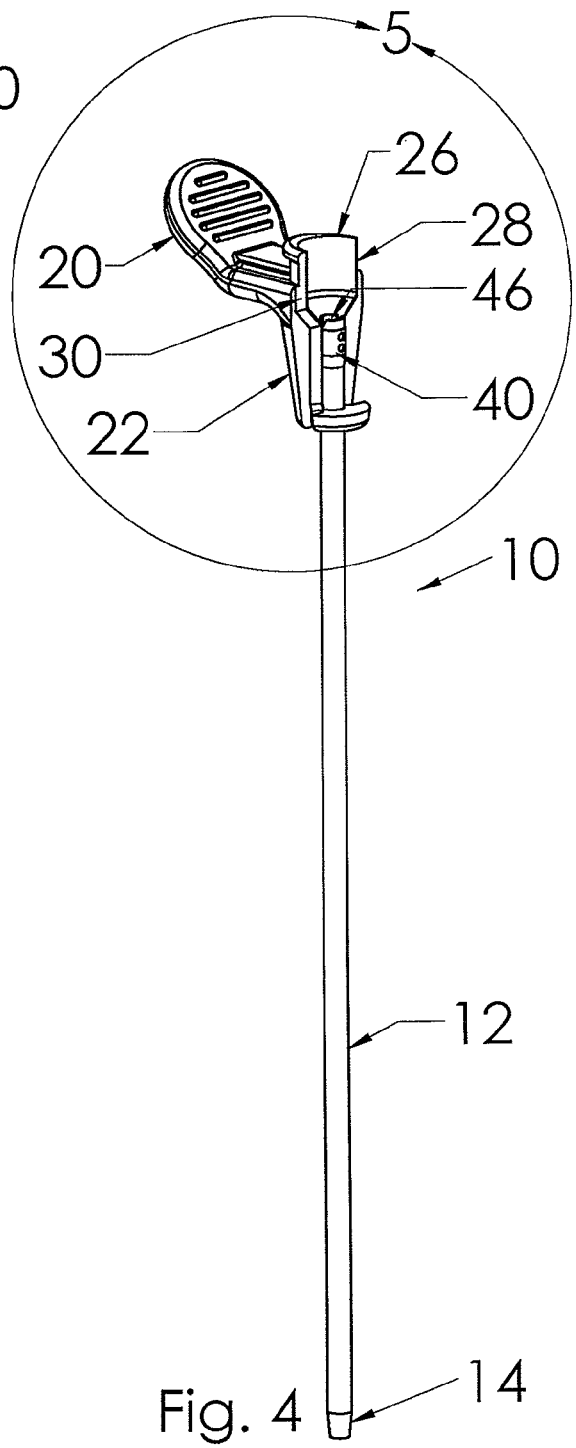
FIG. 4 is a partially sectioned view of the assembly of FIG. 1 with one hub half mostly removed.

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

In FIG. 1, introducer assembly 10 of the present invention includes an elongate sheath tube 12 having a distal end 14 and a passageway extending therethrough, with a hub component 16 affixed to the proximal tube end. Hub component 16 is designed to be manually split, having a body 18 with a pair of tabs 20 each of which is associated with a hub half 22. FIG. 2 shows a dilator 24 in position removably secured to the proximal end portion 26 of the hub component 16 for insertion of distal sheath tube end 14 into an incision into the blood vessel (not shown), after which the dilator 24 will be removed and the distal end of a catheter (not shown) then inserted into the introducer assembly 10. Splitting of the hub component 16 into respective halves 22 is performed after the catheter assembly's distal end portion is within the vasculature of the patient and the two halves of the introducer assembly are torn away.

Now referring to FIGS. 3 to 6, hub 16 is shown to have two hub halves 22 joined to each other by a pair of frangible webs 28 along opposite sides angularly spaced 90° from radial midlines of tabs 20, and V-shaped grooves 30 extending radially outwardly from the webs 28. This particular structure enables the hub 16 to be easily manually split apart by prying apart the tabs 20.

The present invention is directed to facilitating the tearing of the elongate introducer sheath simultaneously with the splitting apart of the hub component 16 into respective halves 22. In FIGS. 7 to 9 are shown one manner of defining a joint between the elongate sheath tube 12 and the hub component 16, wherein discrete joints are defined between the sheath tube and the respective hub halves 22. The proximal end portion 40 of the sheath tube 12 is enlarged to have a larger inner diameter, and at least one pair of holes 42,42 is punched or otherwise defined on respective opposite sides of the tube adjacent the proximal tube end 44. The hub halves 22 would each be joined to an interior lining portion within the sheath tube proximal end portion 40, by joints through the at least one pair of holes 42,42. In one method, a previously formed tubular liner 46 is inserted into the enlarged proximal end portion 40, with a proximal liner portion 47 projecting beyond the proximal end 44 of the sheath tube. The liner may be provided with a pair of notches 48 on opposite sides at the proximal end of the proximal liner portion 47 (or longitudinal slits or score lines along opposite sides of the liner, as seen in FIG. 11, or both), to facilitate splitting, although the liner may be sufficiently thin that such notches or their equivalents may not be necessary; if provided, they would be offset about 90° from the pair or pairs of holes 42 in the proximal sheath end portion 40.

Referring to the representation in FIG. 9, the hub component would then be insert molded about the proximal sheath tube end 40' having the liner 46' in position within the mold cavity. The liner would be of a material that is sufficiently compatible, at least, with the material from which the hub would be made, such as polyethylene, that joints 50' would form within holes 42' integral with both the liner 46' and the two hub halves 22', and additionally would bond with the proximal liner portion 47' at annular joint 51' (without filling in notches 48'), and thus assuredly mechanically securing the sheath tube to the hub component thereby.

The proximal end of the introducer assembly 10 is shown in FIG. 10, after the molding of the hub component 16 to the sheath tube 12 and liner 46. A joint 50' is seen protruding through hole 42 to join one of the sheath halves 22 to the liner 46.

Figure 11:
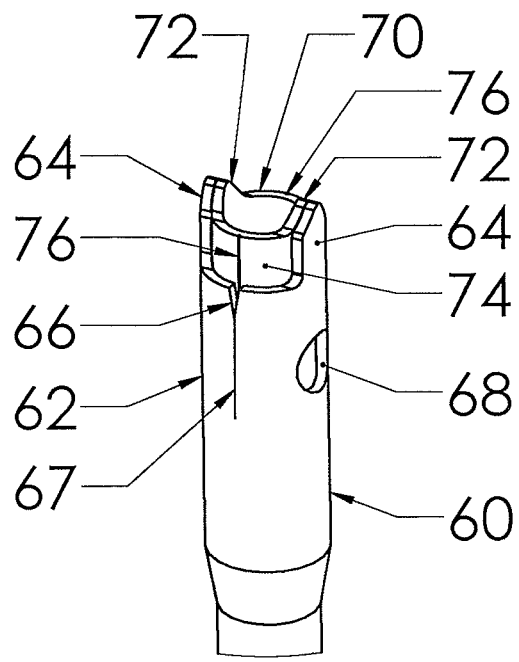
FIG. 11 is an isometric enlarged view of an alternate embodiment of a sheath proximal end with a liner positioned therein, wherein the sheath and liner include complementary ears utilized to properly orient the liner angularly with the sheath tube, for the liner score lines to be aligned with respective notches in the sheath tube proximal end to facilitate initiation of eventual splitting.

An alternative sheath tube 60 is seen in FIG. 11, with an alternative embodiment of liner 70. Expanded proximal sheath tube end 62 includes a pair of proximal projections or ears 64 on opposed sides projecting proximally therefrom. A pair of notches 66 are defined into the proximal end of the sheath tube that will be aligned with frangible webs of the eventual hub component molded thereto, for eventually initiating the splitting of the introducer sheath assembly from a catheter during implantation. Optionally, slits 67 may be defined extending partially along the sheath tube from the notches 66. Holes 68 are formed through the sheath tube exposing the liner 70 therewithin. Liner 70 includes a pair of proximal projections or ears 72 on opposed sides of the proximal liner end portion 74 that can be physically paired with ears 64 of the sheath tube as shown, in order to align score lines 76 (or slits extending partially along the liner) of the liner with notches 66 during introducer sheath assembly manufacturing.

Figure 12:
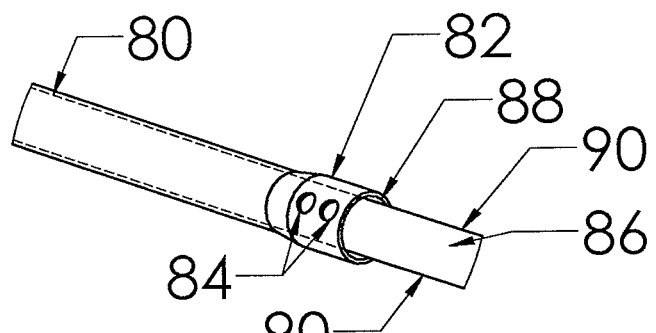
FIG. 12 is an enlarged view of the proximal sheath end without a liner, and associated mandrel that defines an annular gap within the expanded sheath end, for molding a hub component to the sheath end without use of a preformed liner component.

In a variation of the method described above, and referring to FIG. 12, a sheath tube 80 is provided with an enlarged diameter proximal end portion 82, through which at least one pair of opposed holes 84 are formed. A mandrel 86 is inserted through the sheath tube, having an outer diameter equivalent to the inner diameter of the sheath tube, while the expanded proximal sheath end is spaced radially away from the mandrel outer surface. The resultant annular gap 88 permits mold material to fill the holes and form an interior lining portion in the annular gap 88 around the mandrel 86. The mandrel may have pointed longitudinal ridges 90 along opposite sides to define frangible webs in the liner formed during molding, positioned angularly 90° from the location of holes 84,84, all to facilitate eventual splitting during introducer sheath removal.

Preferably, the hub and an interior lining portion can be simultaneously formed integrally joined together for a limited distance just proximally of the sheath tube proximal end. In a further variation of the method described hereinabove, the proximal hub/interior lining portion joint can be in lieu of providing holes through the sheath tube proximal end.

By either method, an effective joint is defined between the hub component and the sheath tube at the proximal end, enabling a sheath tube such as of polytetrafluoroethylene material to have a hub component such as of polyethylene material secured thereto. When such a hub component is eventually split after use, the sheath tube will also tear longitudinally as well, for removal of the introducer sheath from around a catheter.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An introducer sheath assembly, comprising:
    an elongated sheath tube having a distal end and a proximal end and a longitudinal passageway extending therethrough, the sheath tube proximal end having at least one pair of opposed holes therethrough;
    a hub affixed to and extending about at least a portion of an external surface of the proximal end of the sheath tube; and
    an interior lining portion extending along an inside surface of the sheath tube proximal end,
    wherein joints integrally join the hub to the interior lining portion through the at least one pair of opposed holes through the sheath tube adjacent the sheath tube proximal end thereby joining the hub to the elongated sheath tube.

2. The assembly of claim 1, wherein the interior lining portion has an inner diameter generally equal to a diameter of the sheath tube passageway and the diameter of the sheath tube proximal end is expanded for the interior lining portion to be disposed therewithin.

3. The assembly of claim 1, wherein the hub and the interior lining portion are adapted to be manually split apart into associated halves after insertion of a catheter through the introducer sheath, and the elongated sheath tube is adapted to be split upon splitting of the hub and interior lining portion, and respective ones of the at least one pair of opposed joints are joined to respective ones of the hub/lining portion halves.

4. The assembly of claim 3, wherein the elongated sheath tube is formed of a first material, and the hub is formed of a second material different from the first material.

5. The assembly of claim 4, wherein the interior lining portion is a liner preformed of a material at least sufficiently compatible with the second material to form an integral joint therewith during molding of the hub to the elongated sheath tube proximal end.

6. The assembly of claim 5, wherein the liner includes a proximal liner portion projecting proximally from the proximal end of the sheath tube after insertion into the enlarged proximal sheath tube end portion, for eventual bonding with the hub upon molding.

7. The assembly of claim 5, wherein the liner includes score lines extending along opposite sides thereof to facilitate the initiation of splitting thereof for eventual sheath removal.

8. The assembly of claim 5, wherein the liner includes notches extending distally from the proximal end thereof to facilitate the initiation of splitting thereof for eventual sheath removal.

9. The assembly of claim 5, wherein the liner is formed of the second material.

10. The assembly of claim 9, wherein the sheath tube is formed of polytetrafluoroethylene and the hub and liner are formed of polyethylene.

11. The assembly of claim 5, wherein the sheath tube is formed of polytetrafluoroethylene and the hub is formed of polyethylene.

12. The assembly of claim 5, wherein the sheath tube at least includes notches on opposed sides of the proximal end of the proximal portion and further includes proximal projections from the proximal end angularly spaced about 90° from the notch locations, and wherein the liner includes corresponding proximal projections extending from the proximal end thereof similarly angularly spaced about 90° from score lines extending therealong on opposed sides, facilitating appropriate angular orientation between the sheath tube and the liner during molding of the hub component thereto, all to facilitate eventual splitting of the introducer assembly.

13. The assembly of claim 1, wherein the sheath tube proximal end has at least two pairs of opposed holes therethrough, resulting in at least two pairs of opposed joints.

14. A tearaway introducer sheath assembly, comprising:
    an elongated sheath tube having a distal end and a proximal end and a longitudinal passageway extending therethrough, the sheath tube proximal end having at least one pair of opposed holes therethrough;

a hub affixed to and extending about at least a portion of an external surface of the proximal end of the sheath tube; and an interior lining portion extending along an inside surface of the sheath tube proximal end, wherein at least one pair of opposed joints integrally join the hub to the interior lining portion through the at least one pair of opposed holes through the sheath tube adjacent the sheath tube proximal end thereby joining the hub to the elongated sheath tube, and wherein the hub and the interior lining portion are adapted to be manually split apart into associated halves after insertion of a catheter through the introducer sheath, and the elongated sheath tube is adapted to be split upon splitting of the hub and interior lining portion, and respective ones of the at least one pair of opposed joints are joined to respective ones of the hub/lining portion halves.

15. The assembly of claim 14, wherein the elongated sheath tube is formed of a first material, and the hub is formed of a second material different from the first material, and wherein the interior lining portion is a liner preformed of a material at least sufficiently compatible with the second material to form an integral joint therewith during molding of the hub to the elongated sheath tube proximal end.

16. The assembly of claim 15, wherein the sheath tube is formed of polytetrafluoroethylene.

17. The assembly of claim 15, wherein the sheath tube at least includes notches on opposed sides of the proximal end of the proximal portion and further includes proximal projections from the proximal end angularly spaced about 90° from the notch locations, and wherein the liner includes corresponding proximal projections extending from the proximal end thereof similarly angularly spaced about 90° from score lines extending therealong on opposed sides, facilitating appropriate angular orientation between the sheath tube and the liner during molding of the hub component thereto, all to facilitate eventual splitting of the introducer assembly.

18. The assembly of claim 14, wherein the liner includes a proximal liner portion projecting proximally from the proximal end of the sheath tube after insertion into the enlarged proximal sheath tube end portion, for eventual bonding with the hub upon molding.

19. The assembly of claim 18, wherein the liner is formed of the second material.

20. The assembly of claim 19, wherein the sheath tube is formed of polytetrafluoroethylene and the hub and liner are formed of polyethylene.

21. The assembly of claim 14, wherein the liner includes score lines extending along opposite sides thereof to facilitate the initiation of splitting thereof for eventual sheath removal.

22. The assembly of claim 14, wherein the liner includes notches extending distally from the proximal end thereof to facilitate the initiation of splitting thereof for eventual sheath removal.

23. The assembly of claim 14, wherein the sheath tube proximal end has at least two pairs of opposed holes therethrough, resulting in at least two pairs of opposed joints.

* * * * *